United States Patent
Hadden et al.

(12)

(10) Patent No.: US 6,476,255 B1
(45) Date of Patent: Nov. 5, 2002

(54) PRODUCTION OF ESTERS

(75) Inventors: Raymond A Hadden, Durham (GB); Jean M Pearson, Clitheroe (GB)

(73) Assignee: Lucite International UK Limited, Southampton (GB)

( * ) Notice: Subject to any disclaimer, the term of this patent is extended or adjusted under 35 U.S.C. 154(b) by 0 days.

(21) Appl. No.: 09/530,262

(22) PCT Filed: Oct. 12, 1998

(86) PCT No.: PCT/GB98/03074

§ 371 (c)(1),
(2), (4) Date: Nov. 1, 2000

(87) PCT Pub. No.: WO99/21820

PCT Pub. Date: May 6, 1999

(30) Foreign Application Priority Data

Oct. 29, 1997 (GB) ............................................. 9722733

(51) Int. Cl.$^7$ ............................................... C07C 67/38
(52) U.S. Cl. ........................................................ 560/233
(58) Field of Search ......................................... 560/233

(56) References Cited

FOREIGN PATENT DOCUMENTS

| EP | 0 495 548 A2 | 7/1992 |
| WO | 96/19434 | 6/1996 |

*Primary Examiner*—Paul J. Killos
(74) *Attorney, Agent, or Firm*—Pillsbury Winthrop LLP

(57) ABSTRACT

A process for the manufacture of an alkyl ester of an aliphatic carboxylic acid comprises the steps of supplying a first feed stream comprising carbon monoxide and an alkene of formula $C_nH_{2n}$ to a reactor, supplying a second feed stream comprising an alkyl alcohol, having a formula R—OH where R is an optionally substituted alkyl group, to the reactor, and reacting together said first and second feed streams in the reactor in the presence of a carbonylation catalyst, which catalyses the carbonylation reaction between carbon monoxide and the alkene, to form a product comprising an alkyl alkanoate having the formula $C_nH_{2n+1}COOR$, such that the ratio of alkyl alcohol to alkyl alkanoate present in the reactor is greater than the ratio of alkyl alcohol to alkyl alkanoate present in an azeotropic mixture of the alkyl alcohol and alkyl alkanoate. The process is particularly useful for the manufacture of methyl propionate by the methoxycarbonylation of ethylene.

13 Claims, No Drawings

PRODUCTION OF ESTERS

The present invention concerns a process for the production of alkyl esters of aliphatic carboxylic acids, in particular methyl propionate, from alkene, carbon monoxide and alkanol.

The production of alkanoic esters and acids by carbonylation of alkenes in the presence of an alkanol or water, as appropriate, is well known. The carbonylation of ethylene using carbon monoxide in the presence of an alcohol or water and a catalyst system comprising a Group VIII metal, e.g. palladium, and a phosphine ligand, e.g. an alkyl phosphine, cycloalkyl phosphine, aryl phosphine, pyridyl phosphine or bidentate phosphine, has been described in numerous European patents and patent applications, e.g. EP-A-0055875, EP-A0489472, EP-A-0106379, EP-A-0235864, EP-A-0274795, EP-A0499329, EP-A-0386833, EP-A-0441447, EP-A-0282142, EP-A-0227160, EP-A-0495547 and EP-A-0495548 and in WO97/03943.

EP-A-0411721 discloses a continuous process for the preparation of an alkyl propionate, which comprises reacting an alkanol in a liquid phase with ethylene and carbon monoxide in a reaction vessel in the presence of a carbonylation catalyst and passing a gas through the reaction vessel, thereby forming a stream of vapour comprising alkyl propionate, gas and unreacted alkanol. The vapour stream is then condensed and the resulting liquid comprises alkyl propionate, alkanol and impurities. The alkanol or alkanol/alkyl propionate azeotropic mixture is distilled off the alkyl propionate product stream and recycled to the reaction vessel.

In the production of methyl propionate from ethylene, carbon monoxide and methanol described in EP-0411721-A, the ratio of methyl propionate product to methanol in the reactor is greater than 50:50 mole %. For example, methanol and other alkanol levels of 18–20% are used. This is not surprising because methanol and methyl propionate form an azeotropic mixture comprising approximately 50 wt % of each component and it may therefore be expected that operating the process such that the composition of the reaction mixture, and thus the product stream, is richer in methyl propionate than methanol, i.e. operating with a composition on the methyl propionate side of the azeotrope, would be beneficial because separation of the methyl propionate product from the residual methanol in the product stream may then be achieved by means of a simple distillation.

Consideration of published information concerning such reactions confirms that it is usual to operate with the ratio of methyl propionate to methanol as described above.

Surprisingly we have found that superior results are obtained if the reaction in the reactor takes place with a concentration of reactant alcohol relative to product ester substantially in excess of that level of alcohol which would form an azeotrope with the ester.

According to the invention a process for the manufacture of an alkyl ester of an aliphatic carboxylic acid comprises the steps of:
a) supplying a first feed stream comprising carbon monoxide and an alkene of formula $C_nH_{2n}$ to a reactor;
b) supplying a second feed stream comprising an alkyl alcohol of formula R—OH, where R is an alkyl group, to the reactor,
c) reacting together said first and second feed streams in the reactor in the presence of a carbonylation catalyst, which catalyses the carbonylation reaction between carbon monoxide and the alkene, to form a product comprising an alkyl alkanoate having the formula $C_nH_{2n+1}COOR$,
characterised in that the ratio of alkyl alcohol to alkyl alkanoate present in the reactor is greater than the ratio of alkyl alcohol to alkyl alkanoate present in an azeotropic mixture of the alkyl alcohol and alkyl alkanoate.

The carbon monoxide may be used in the presence of other gases which are inert in the reaction. Examples of such gases include hydrogen, nitrogen, carbon dioxide and the noble gases such as argon.

The first feed stream may be fed as a gaseous phase.

The first feed stream and the second feed stream may be fed to the reactor separately or together.

The alkene preferably comprises ethylene. The molar ratio of the ethylene to carbon monoxide in the gaseous phase is preferably greater than 1:1, more preferably at least 3:1, especially from 3:1 to 50:1 and most preferably in the range from 3:1 to 15:1.

Suitable alkyl alcohols include $C_{1-30}$ alkanols, optionally substituted with one or more substituents such as halogen atoms, cyano, carbonyl, alkoxy or aryl groups. Suitable alkanols include one or more of methanol, ethanol, propanol, 2-propanol, 2-butanol, t-butyl alcohol and chlorocapryl alcohol. Particularly useful are methanol and ethanol. Additionally or alternatively, polyhydroxyl compounds, such as diols and sugars, may be used. The preferred alkyl alcohol is methanol.

Thus in a preferred form of the invention, we provide a process for the manufacture of methyl propionate comprising the steps of:
a) supplying a first feed stream comprising carbon monoxide and ethylene in the gas phase to a reactor;
b) supplying a second feed stream comprising methanol to the reactor;
c) reacting together said first and second feed streams in the reactor in the presence of a carbonylation catalyst, which catalyses the carbonylation reaction between carbon monoxide and ethylene, to form a product comprising methyl propionate;
characterised in that the ratio of methanol to methyl propionate present in the reactor is greater than 47:53 weight %.

The carbonylation catalyst preferably comprises a combination of palladium or a compound thereof and phosphorous-containing compound. Various phosphine compounds are suitable catalysts and have been described in prior publications, e.g. tertiary phosphines of general formula $R^1R^2R^3$ P wherein $R^1$, $R^2$ and $R^3$ are each an optionally substituted alkyl or aryl group, e.g. tri-phenyl phosphine. A particularly preferred phosphorous-containing compound is a bidentate phosphine ligand of general formula $(R_3—C)_2P—L^1—X—L^2—P—(C—R_3)_2$, in which each R is independently a pendant, optionally substituted, organic group through which the group is linked to tertiary carbon atom C; $L^1$, $L^2$ are independently a linking group selected from an optionally substituted lower alkylene chain connecting the respective phosphorous atom to the group X and X is a bridging group comprising an optionally substituted aryl moiety to which the phosphorous atoms are linked on available adjacent carbon atoms. Such a catalyst is described in WO/96/19434.

The pendant optionally substituted organic groups, R, may be independently selected from a wide range of components. Preferably, the pendant groups are optionally substituted lower alkyl, e.g. $C_{1-8}$, and which may be branched or linear. Particularly preferred is when the organic groups, R, when associated with their respective carbon atom form composite groups which are at least as sterically hindering as t-butyl. Steric hindrance in this context is as discussed at page 14 et seq of "Homogeneous Transition Metal Catalysis—A Gentle Art", by C Masters, published by Chapman and Hall, 1981.

The linking groups, $L^1$ and $L^2$, are independently selected from an optionally substituted, particularly lower alkyl, e.g. $C_1$ to $C_4$, substituted, lower alkylene, e.g. $C_1$ to $C_4$ chain. Especially preferred is when both $L^1$ and $L^2$ are methylene.

Optional substitution of the aryl moiety, X, may be by other organic groups, e.g. alkyl, particularly $C_{1-8}$, aryl, alkoxy, carbalkoxy, halo, nitro, trihalomethyl and cyano. Furthermore, the aryl moiety may be a fused polycyclic group, e.g. naphthalene, biphenylene or indene.

Examples of suitable bidentate ligands are bis (di-t-butyl phosphino)-o-xylene (also known as 1,2 bis (di-t-butylphosphinomethyl)benzene), bis (di-t-neopentyl phosphino)-o-xylene and bis 1,2(di-t-butyl phosphino) naphthalene. Additionally, the bidentate phosphine may be bonded to a suitable polymeric or inorganic substrate via at least one of the bridging group X, the linking group $L^1$ or the linking group $L^2$, e.g. bis (di-t-butyl phosphino)-o-xylene may be bonded via the xylene group to polystyrene to give an immobile heterogeneous catalyst.

The amount of bidentate ligand used can vary within wide limits. Preferably, the bidentate ligand is present in an amount such that the ratio of the number of moles of the bidentate ligand present to the number of moles of palladium present is from 1 to 50, e.g. 1 to 10 and particularly from 1 to 5 mol per mol.

Preferably an additional compound comprising an anion which is essentially non-coordinating to palladium ions is also present in the reaction mixture. The anion may be introduced as one or more of an acid having a pKa measured in aqueous solution of less than 4, a salt with a cation that does not interfere with the reaction, e.g. metal salts or largely organic salts such as alkyl ammonium, and a precursor, such as an ester, that can break down under reaction conditions to generate the anion in situ and acids derived from interactions between Lewis acids and Broensted acids such as $SbCl_4^-$, $FeCl_4^-$ and other similar compounds. . Suitable acids and salts include the acids and salts, other than unsubstituted carboxylates, listed supra. A preferred source of an anion is methanesulphonic acid.

The molar ratio of anion to palladium may be from 1:1 to 500:1, preferably from 2:1 to 100:1 and particularly from 3:1 to 30:1. The anion may be provided by a combination of acid and salt.

Suitable compounds of palladium include salts of palladium with, or compounds comprising weakly coordinated anions derived from nitric acid; sulphuric acid; lower alkanoic (up to $C_{12}$) acids such as acetic acid and propionic acid including halogenated carboxylic acids such as trifluoroacetic acid and trichloroacetic acid; sulphonic acids such as methanesulphonic acid, chlorosulphonic acid, fluorosulphonic acid, trifluoro methanesulphonic acid, benzenesulphonic acid, naphthalenesulphonic acid, toluenesulphonic acids, e.g. p-toluenesulphonic acid, t-butylsulphonic acid, and 2-hydroxypropanesulphonic acid; sulphonated ion exchange resins; perhalic acids such as perchloric acid; halogenated carboxylic acids such as trichloroacetic acid and trifluoroacetic acid; orthophosphoric acid; phosphonic acids such as benzenephosphonic acid; and acids derived from interactions between Lewis acids and Broensted acids. Other sources which may provide suitable anions include the optionally halogenated tetraphenylborate derivatives, e.g. perfluorotetraphenyl borate. Additionally, zero-valent palladium complexes particularly those with labile ligands, e.g. alkenes such as dibenzylideneacetone or styrene may be used.

The catalyst system may be used homogeneously or heterogeneously. Preferably the catalyst system is used homogeneously. The catalyst system is preferably constituted in the liquid phase which may be formed by one or more of the reactants or by the use of a suitable solvent.

Suitable solvents that may be used in conjunction with the catalyst system include one or more aprotic solvents such as ethers, e.g. diethyl ether, dimethyl ether of diethylene glycol, anisole and diphenyl ether; aromatic compounds, including halo variants of such compounds, e.g. benzene, toluene, ethyl benzene, o-xylene, m-xylene, p-xylene, chlorobenzene, o-dichlorobenzene, m-dichlorobenzene, and p-dichlorobenzene; alkanes, including halo variants of such compounds, e.g. hexane, heptane, 2,2,3-trimethylpentane, methylene chloride and carbon tetrachloride; nitriles, e.g. benzonitrile and acetonitrile; esters, e.g. methyl benzoate, methyl acetate, methyl propionate and dimethyl phthalate; sulphones, e.g. diethyl sulphone and tetrahydrothiophene 1,1-dioxide; carboxylic acids, e.g. propionic acid. Particularly suitable solvents are the reactants and products of the reaction. Therefore in the carbonylation of ethylene with carbon monoxide in the presence of methanol to form methyl propionate, preferred solvents are methyl propionate and methanol.

The process of the present invention is preferably carried out at a temperature from 20 to 250° C., in particular from 40 to 150° C. and especially from 70 to 120° C.

The process may be conducted under a total pressure of from $1 \times 10^5$ to $100 \times 10^5$ $N.m^{-2}$ and in particular from $5 \times 10^5$ to $50 \times 10^5$ $N.m^{-2}$.

Contrary to the mode of operating the process which is suggested in the prior art, we have found that it is beneficial to operate the process with a ratio of concentration of methanol to methyl propionate which is on the methanol-rich side of the methanol/methyl propionate azeotrope. When the reaction proceeds at a high rate the turnover number (TON) of the catalyst may be maximised. Therefore the operation of the reaction at relatively high concentrations of methanol enables the catalyst life to be maximised and the cost of catalyst per quantity of methyl propionate produced to be reduced. When the catalyst is relatively expensive, the saving in catalyst costs may be substantial.

The reaction is preferably operated continuously, however batch operation is possible. In a continuous process, the ratio of concentration of methanol to methyl propionate in the reactor and therefore in the product stream is in the range from 47:53 wt % to 99:1 wt %, preferably in the range 55:45 to 95:5 wt % and more preferably in the range 55:45 to 85:15 wt %.

The methyl propionate product may be obtained from the product stream by a separation method such as distillation. Methyl propionate and methanol form an azeotropic mixture comprising 47 wt % of methanol and 53 wt % of methyl propionate. Therefore in a distillation process to obtain methyl propionate from a mixture of methanol and methyl propionate which contains greater than 47 wt % of methanol simple distillation is not possible and it is necessary to employ a technique to break the azeotrope. It is therefore preferred to separate the methyl propionate from the product stream by distillation in the presence of an entrainer compound.

The invention is further illustrated in the following Examples:

EXPERIMENTAL METHOD 0.037 g ($5.03 \times 10^{-5}$ moles) of a solid catalyst, Pd (di-t butylphosphino o-xylene) diberzylidene acetone, was weighed into a flask under nitrogen in a drybox. Methyl propionate was deoxygenated with nitrogen in a syringe then added to the palladium complex in the flask with stirring, followed by methanol. 0.068 ml (1.05×10$^{-3}$ moles) methanesulphonic acid was then added directly to the solution. The solution was transferred to a two-liter stainless steel autoclave by suction through a sample line to avoid air exposure.

The autoclave and solution were then heated to 80° C. over a period of approximately thirty minutes. When at temperature a 1:1 mixture of carbon monoxide and ethylene was added up to a pressure of 10 barg.

The autoclave was set up as a semi-continuous batch system—the gases were continuously fed to the system via a regulator, keeping the autoclave at a constant pressure, but no new liquid reactants were added or product removed. The gases were fed from a ten liter reservoir, and the extent and rate of reaction was obtained from the amount and speed with which the gas was used up from this reservoir.

EXAMPLES 1–5

The above described procedure was carried out at different ratios of methanol to methyl propionate, which are shown in Table 1 below. The table also shows the amount of methyl propionate formed and the turnover number of the catalyst after 4 hours.

TABLE 1

| Example | MeP (ml) | MeOH (ml) | Concentration Ratio (Wt % MeOH: Wt % MeP) | Mol MeP formed in 4 hrs | TON (mol MeP/mol Pd in 4 hrs) | Initial reaction rate (mol MeP/ mol Pd/hr) |
|---|---|---|---|---|---|---|
| 1 | 26 | 274 | 90:10 | 1.003 | 19946 | 36679 |
| 2 | 81 | 219 | 70:30 | 0.579 | 11507 | 33209 |
| 3 | 139 | 161 | 50:50 | 0.602 | 11976 | 18093 |
| 4 | 200 | 100 | 30:70 | 0.377 | 7330 | 8008 |
| 5 | 233 | 67 | 20:80 | 0.133 | 2642 | 2692 |

The results clearly show that at ratios of concentrations of MeOH to MeP of less than 50:50 weight %, the turnover number of the catalyst and the amount of MeP produced in the 4-hour duration of the experiment was considerably reduced relative to the catalyst turnover and production of MeP achieved at lower higher ratios of MeOH to MeP (i.e. higher proportions of MeOH in the reaction mixture).

What is claimed is:

1. A continuous process for the manufacture of an alkyl ester of an aliphatic carboxylic acid comprising the steps of:
   a) supplying a first feed stream comprising carbon monoxide and an alkene of formula $C_nH_{2n}$ to a reactor;
   b) supplying a second feed stream comprising an alkyl alcohol, having a formula R—OH where R is an optionally substituted alkyl group, to the reactor;
   c) reacting together said first and second feed streams in the reactor in the presence of a carbonylation catalyst, which catalyses the carbonylation reaction between carbon monoxide and alkene, to form a product comprising an alkyl alkanoate having the formula $C_nH_{2n+1}COOR$ characterised in that the ratio of alkyl alcohol to alkyl alkanoate present in the reactor is greater than the ratio of alkyl alcohol to alkyl alkanoate present in an azeotropic mixture of the alkyl alcohol and alkyl alkanoate.

2. A process for the manufacture of an alkyl ester of an aliphatic carboxylic acid comprising the steps of:
   a) supplying a first feed stream comprising carbon monoxide and an alkene of formula $C_nH_{2n}$ to a reactor;
   b) supplying a second feed stream comprising an alkyl alcohol, having a formula R—OH where R is an optionally substituted alkyl group, the reactor;
   c) reacting together said first and second feed streams in the reactor in the presence of a carbonylation catalyst, which catalyses the carbonylation reaction between carbon monoxide and the alkene, to form a product comprising an alkyl alkanoate having the formula $C_nH_{2n+1}COOR$ characterised in that the ratio of alkyl alcohol to alkyl alkanoate present in the reactor is greater than the ratio of alkyl alcohol to alkyl alkanoate present in an azeotropic mixture of the alkyl alcohol and alkyl alkanoate.

3. A process as claimed in claim 1 or 2, wherein the alkene comprises ethylene.

4. A process as claimed in any preceding claim, wherein the alkyl alcohol comprises $C_{1-30}$ alkanols, optionally substituted with one or mote substituents.

5. A process as claimed in claim 4, wherein the alkyl alcohol comprises methanol.

6. A continuous process for the manufacture of methyl propionate comprising the steps of:
   a) supplying a first feed stream comprising carbon monoxide and ethylene in the gas phase to a reactor;
   b) supplying a second feed stream comprising methanol to the reaction;
   c) reacting together said first and second feed streams in the reactor in the presence of a carbonylation catalyst, which catalyses the carbonylation reaction between carbon monoxide and ethylene, to form a product comprising methyl propionate;

characterised in that the ratio of methanol to methyl propionate present in the reactor is in the range from 47:53–99:1 weight %.

7. A process for the manufacture of methyl propionate comprising the steps of:
   a) supplying a first feed stream comprising carbon monoxide and ethylene in the gas phase to a reactor;
   b) supplying a second feed stream comprising methanol to the reactor;
   c) reacting together said first and second feed streams in the reactor in the presence of a carbonylation catalyst, which catalyses the carbonylation reaction between carbon monoxide and ethylene, to form a product comprising methyl propionate;

characterised in that the ratio of methanol to methyl propionate present in the reactor is in the range from 47:53–99:1 weight %.

8. A process as claimed in claim 6 or 7, Wherein the ratio of concentration of methanol to methyl propionate in the reactor is in the range 55:45 to 95:5 wt %.

9. A process as claimed in claim 6 or 7 wherein the ratio of the concentration of methanol to methyl propionate in the reactor is in the range 55:45 to 85:15 wt %.

10. A process as claimed in claim 6 or claim 7, wherein the carbonylation catalyst comprises a combination of palladium or a compound thereof and phosphorous-containing compound.

11. A process as claimed in claim 10, wherein the phosphorous-containing compound is a bidentate phosphine ligand of general formula $(R_3—C)_2P—L^1—X—L^2—P—(C—R_3)_2$, in which each R is independently a pendant, optionally substituted, organic group through which the group is linked to tertiary carbon atom C; $L^1$, $L^2$ are independently a linking group selected from an optionally substituted lower alkylene chain connecting the respective phosphorous atom to the group X and X is a bridging group comprising an optionally substituted aryl moiety to which the phosphorous atoms are linked on available adjacent carbon atoms.

12. A process as claimed in claim 1 or claim 2, wherein the carbonylation catalyst comprises a combination of palladium or a compound thereof and phosphorous-containing compound.

13. A process as claimed in claim 12, wherein the phosphorous-containing compound is a bidentate phosphine ligand of general formula $(R_3C)_2P—L^1—X—L^2—P—(C—R_3)_2$, in which each R is independently a pendant, optionally substituted, organic group through which the group is linked to tertiary carbon atom C; $L^1$, $L^2$ are independently a linking group selected from an optionally substituted lower alkylene chain connecting the respective phosphorous atom to the group X and C is a bridging group consisting of an optionally substituted aryl moiety to which the phosphorous atoms are linked on available carbon atoms.

\* \* \* \* \*